US 12,171,497 B2

(12) United States Patent
Mäkkeli et al.

(10) Patent No.: US 12,171,497 B2
(45) Date of Patent: Dec. 24, 2024

(54) APPARATUS FOR MEASURING INTRAOCULAR PRESSURE

(71) Applicant: ICARE FINLAND OY, Vantaa (FI)

(72) Inventors: Pauliina Mäkkeli, Espoo (FI); Rami Haulisto, Vantaa (FI); Matti Raudasoja, Vantaa (FI); Jussi Pukki, Helsinki (FI); Teemu Herranen, Hyvinkää (FI); Ari Kukkonen, Helsinki (FI); Mika Salkola, Espoo (FI)

(73) Assignee: ICARE FINLAND OY, Vantaa (FI)

( * ) Notice: Subject to any disclaimer, the term of this patent is extended or adjusted under 35 U.S.C. 154(b) by 276 days.

(21) Appl. No.: 16/062,160

(22) PCT Filed: Dec. 14, 2016

(86) PCT No.: PCT/FI2016/050871
§ 371 (c)(1),
(2) Date: Jun. 14, 2018

(87) PCT Pub. No.: WO2017/103330
PCT Pub. Date: Jun. 22, 2017

(65) Prior Publication Data
US 2018/0368681 A1    Dec. 27, 2018

(30) Foreign Application Priority Data

Dec. 18, 2015  (FI) ...................................... 20155973

(51) Int. Cl.
*A61B 3/16*     (2006.01)
*G01R 1/067*    (2006.01)

(52) U.S. Cl.
CPC ............ *A61B 3/16* (2013.01); *G01R 1/06788* (2013.01)

(58) Field of Classification Search
CPC ...... A61B 3/165; A61B 3/16; G01R 1/06794; G01R 1/06788
See application file for complete search history.

(56) References Cited

U.S. PATENT DOCUMENTS 3,308,653 A * 3/1967 Roth ........................ A61B 3/16
                                                      600/402
3,763,696 A * 10/1973 Krakau ..................... A61B 3/16
                                                      600/402

(Continued)

FOREIGN PATENT DOCUMENTS

| CN | 104274153 A | 1/2015 |
| JP | 2005529670 A | 10/2005 |

(Continued)

OTHER PUBLICATIONS

Finnish Search Report issued by the Finnish Patent and Registration Office in relation to Finnish Patent Application No. 20155973 dated Jun. 7, 2016 (2 pages).

(Continued)

*Primary Examiner* — Rene T Towa
*Assistant Examiner* — H. Q. Nguyen
(74) *Attorney, Agent, or Firm* — Robert P. Michal, Esq.; Carter, DeLuca & Farrell LLP

(57) ABSTRACT

A device for measuring intraocular pressure includes a functional part with a tubular probe base and a probe contactable with a surface of an eye to derive an intraocular pressure in the eye from variations in a velocity of the probe. The probe is inside the tubular probe base. The probe is partly formed of magnetic material. An induction coil gives the probe a specific velocity. The device also has means for measuring the variations in a velocity of the probe, means for processing and displaying the measurement data, and controlling operations. The device is mainly characterized (Continued)

Figure 2:
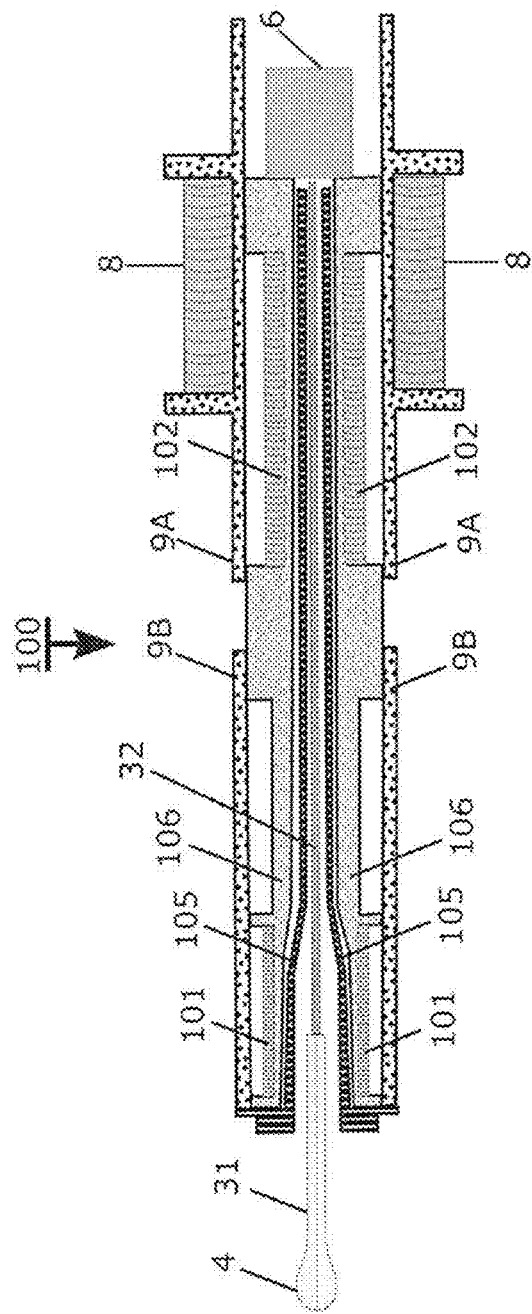

by means for holding the probe inside the tubular probe base, and means for releasing the probe for the measurement.

19 Claims, 9 Drawing Sheets

(56) References Cited

U.S. PATENT DOCUMENTS

| | | | |
|---|---|---|---|
| 5,148,807 A | | 9/1992 | Hsu |
| 5,165,409 A | * | 11/1992 | Coan .................. A61B 3/16 600/401 |
| 5,176,139 A | | 1/1993 | Fedorov et al. |
| 5,251,627 A | * | 10/1993 | Morris ................ A61B 3/165 600/398 |
| 5,279,300 A | | 1/1994 | Miwa et al. |
| 5,299,573 A | | 4/1994 | Kobayashi |
| 6,093,147 A | * | 7/2000 | Kontiola .............. A61B 3/16 600/405 |
| 6,394,954 B1 | | 5/2002 | Piletsky et al. |
| 9,155,467 B1 | * | 10/2015 | Enikov ................ A61B 3/16 |
| 2005/0137473 A1 | | 6/2005 | Kontiola |
| 2005/0137474 A1 | * | 6/2005 | Kontiola .............. A61B 3/16 600/398 |
| 2008/0103381 A1 | * | 5/2008 | Kontiola .............. A61B 3/16 600/405 |
| 2009/0306493 A1 | * | 12/2009 | Kontiola .............. A61B 3/16 600/399 |

FOREIGN PATENT DOCUMENTS

| | | |
|---|---|---|
| JP | 2010087062 A | 4/2010 |
| JP | 2011167570 A | 9/2011 |
| JP | 7265866 B2 | 4/2023 |
| WO | WO-03105681 A1 | 12/2003 |
| WO | WO-2006067266 A1 | 6/2006 |

OTHER PUBLICATIONS

International Search Report issued by the European Patent Office acting as the International Searching Authority in relation to International Application No. PCT/FI2016/050871 dated Mar. 27, 2017 (4 pages).

Written Opinion of the International Searching Authority issued by the European Patent Office acting as the International Searching Authority in relation to International Application No. PCT/FI2016/050871 dated Mar. 27, 2017 (6 pages).

Japanese Office Action dated Sep. 16, 2020, issued in corresponding Japanese Application No. 2018-531525, 10 pages, including translation.

Japanese Office Action (5 pages) and English Translation (3 pages) dated Jan. 18, 2023, issued in corresponding Japanese Application No. 2022-026431, 8 pages total.

Japanese 2nd Office Action dated Jul. 13, 2023 (4 pages) and English translation (3 pages), issued in corresponding JP Appln. No. 2022-026431, 7 pages total.

\* cited by examiner

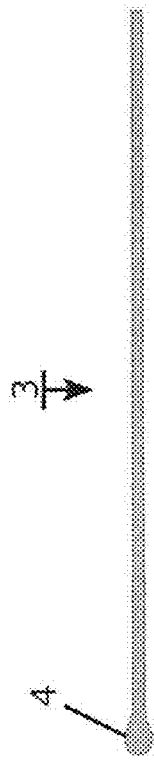
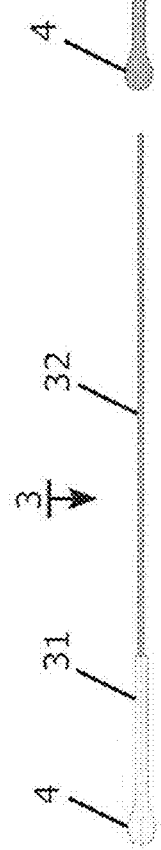
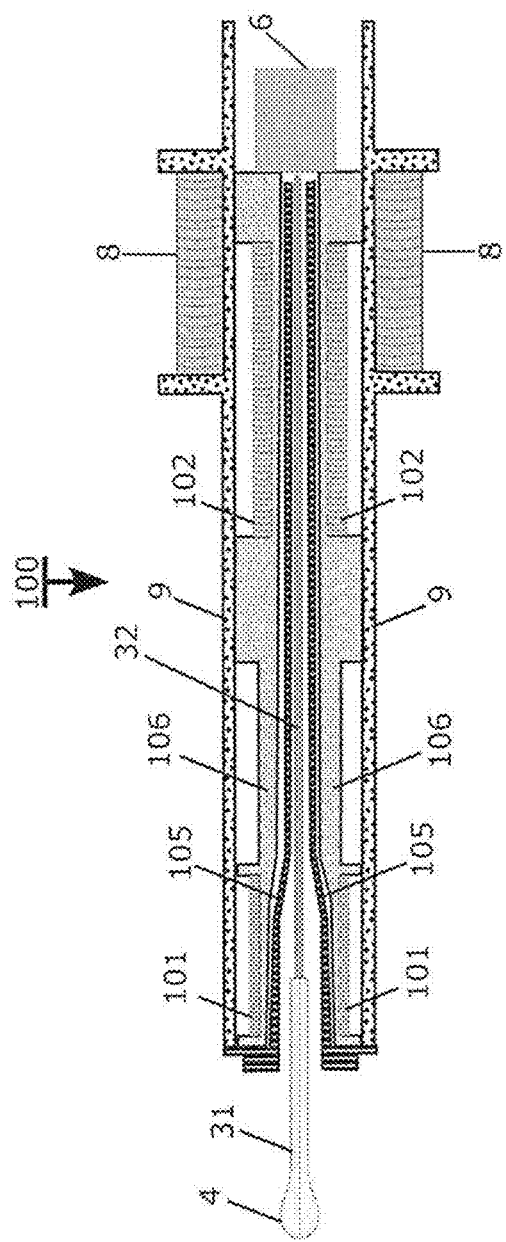
Figure 1A
Figure 1B
Figure 1C

APPARATUS FOR MEASURING INTRAOCULAR PRESSURE

CROSS-REFERENCE TO RELATED APPLICATIONS

This application is a national phase entry under 35 U.S.C. 371 of PCT International Application No. PCT/FI2016/050871 filed Dec. 14, 2016, which claims priority to Finnish Patent Application No. 20155973, filed Dec. 18, 2015, the disclosure of each of these applications is expressly incorporated herein by reference in their entirety.

TECHNICAL FIELD

The invention is concerned with an apparatus for measuring intraocular pressure. It comprises a functional part with a tubular probe base and a probe contactable with a surface of an eye to derive an intraocular pressure in the eye from variations in a velocity of the probe, which is inside the tubular probe base. The probe is partly of magnetic material. An induction coil gives the probe a specific velocity. The apparatus also has means for measuring the variations in a velocity of the probe, means for processing and displaying the measurement data, controlling operations, means for holding the probe (3) inside the tubular probe base, and means for releasing the probe for the measurement.

BACKGROUND

Tonometry is a method for measuring intraocular pressure and the apparatus used for the measurements is called tonometer. Various types of tonometers exist. In contact tonometry, there is a physical contact with the cornea during measurement. A probe is directed against the surface of the cornea, the elasticity of which is measured using various methods. The Goldmann tonometer and the Schiotz tonometer are examples of tonometers.

Two of the most commonly used principles are the measurement of the force required to applanate a certain area of the surface of the eye, or the measurement of the diameter of the area that is applanated by a known force. These methods require the patient's cooperation and cannot be applied without general anaesthesia.

Methods, such as those presented in US patent publications, U.S. Pat. Nos. 5,148,807, 5,279,300, and 5,299,573, in which the surface of the cornea is not touched, the intraocular pressure is instead measured with the aid of a water or air jet, or various kinds of waves, have also been developed. These methods are technically complex and thus expensive. Meters operating on the air-jet principle are widely used by opticians, but their cost has prevented them from being more extensively used by general practitioners.

Rebound tonometry is a type of contact tonometry, wherein a probe, which is partly of magnetic material is accelerated towards an eye by means of an inductive coil system. Upon contact with the cornea of the eye, the probe starts to decelerate and rebounds from the eye. As a result, a voltage is induced in an other coil and the intraocular pressure is calculated from measurement data of parameters of the moving.

U.S. Pat. No. 6,093,147 is mentioned as prior art for such a tonometer. It comprises a probe, which is propelled at a constant velocity in the horizontal direction to impact the eye and includes a device for continuously determining the velocity of the probe. The tonometer disclosed is suitable for horizontal measurements.

The problem with the rebound tonometers of prior art is that measurements, in which the probe in the tonometer apparatus moves in an inclined direction, are not possible to make securely since the probe tend to fall from the apparatus when it is inclined. This means that the measurements have to be done with the patient in upright position if the probe is not prevented from falling by e.g. mechanical means and/or by regulating the driving current and using a wide probe holder, which prevents the probe from falling from the device.

However, in some situations, it is necessary to perform intraocular pressure measurements when the patient is in a non-vertical position, such as during eye surgery. Consequently, an inclined measurement, especially a vertical measurement, is a very useful and desired feature in tonometry.

US patent publication 5176139 discloses a method based on rebound technology, in which a freely-falling ball is dropped onto the eyelid and the height of the ball's rebound is measured. The amount of the ball rebound varies depending on the amount of intraocular pressure and the latter is judged against the amount of the ball rebound. The method solves the above problem mechanically by having a spring lock to prevent the ball from falling and keep it in the top most position. Upon depressing the spring lock, the ball is released for the measurement. The patient can be either recumbent (by leaning back) or sitting during the measurement.

CN patent publication 104274153A is mentioned as prior art for a soft touch intraocular pressure horizontal or vertical measuring device and method, the device comprising a small magnetic needle pressure measuring probe, a front end device, and a driving adjusting circuit. The device has a magnetic induction coil connected with an electric solenoid skeleton that is provided with a permanent magnet and an iron core. When the power is on, the probe can be prevented from falling during a vertical measurement by introducing currents in the coils.

There is, however, need for a tonometer device, wherein the probe stays inside the tonometer whether the power is on or off. Also, there is need for a tonometer device, wherein the movement of a rebound type probe can be more easily controlled in all kind of measurements.

SUMMARY

The apparatus of the invention for measuring intraocular pressure comprises a functional part with a tubular probe base and a probe contactable with a surface of an eye to derive an intraocular pressure in the eye from variations in a velocity of the probe. The probe is inside the tubular probe base. The probe is partly of magnetic material. An induction coil gives the probe a specific velocity. The apparatus also has means for measuring the variations in a velocity of the probe, means for processing and displaying the measurement data, controlling operations, means for holding the probe inside the tubular probe base, and means for releasing the probe for the measurement. The apparatus is mainly characterized in that the means for holding the probe is a magnetic circuit and the means for releasing the probe is a magnetic coil.

The preferable embodiments of the invention have the features of the subclaims.

With inclined measurements is meant measurements in which the measurements are performed with the tonometer in such a position that the probe is during measurement moving in a direction forming an angle compared to the horizontal plane. Vertical measurements, wherein this angle is 90°, is to be seen as a special case of an inclined measurement, in which the measurements are performed with the tonometer in such a position that the probe is moving vertically during measurement (i.e. perpendicularly to the horizontal plane).

Currently, in the rebound tonometer apparatuses of prior art, the probe does not fall from the tonometer when the power is on even if the apparatus is inclined because the measuring coil is pulling the probe back. However, the clinicians performing the measurement might not remember to switch the power on before inclining the apparatus for the measurement, which is a risk for the patient to get the probe in the eye if there is no additional means to prevent the probe from falling.

In the apparatus of the present invention, vertical and other inclined measurements are risk-free thanks to the inventive means for holding the probe inside the tonometer in a probe base. The probe stays inside the probe base of the tonometer independently of whether the power is on or off.

The means for holding the probe inside the probe base can e.g. be a magnetic circuit like in the invention, or it can be a mechanical lock, or a friction brake.

In the developing of the apparatus of the invention, the focus has been in the control of the influence of gravity on the probe. With the apparatus of the invention, an inclined/vertical measurement can be performed by decreasing the driving current as a function of the inclination degree because the influence of gravity on the probe also changes as a function of the inclination degree.

The intraocular pressure is determined from the movement parameters, which are examined from the induced voltage in the measuring coil.

The improvement of the invention of holding the probe inside the probe base during inclined/vertical measurement also when the power is off improves the usability of the device. Yet, the invention retains the apparatus' as a simple, economical, and precise measuring basic construction by means of which intraocular pressure also can be measured in patients incapable of co-operating. In addition, the apparatus of the invention is also suitable for extensive screening campaigns, as the measurements are rapid and require neither local anaesthesia nor specially trained operators. The position of the apparatus during the measurements is now more flexible including the possibility for both horizontal and inclined/vertical measurements in a secure way.

Next, the invention will be described by means of some example embodiments and accompanying figures to which the invention is not restricted.

FIGURES

Figure 3:
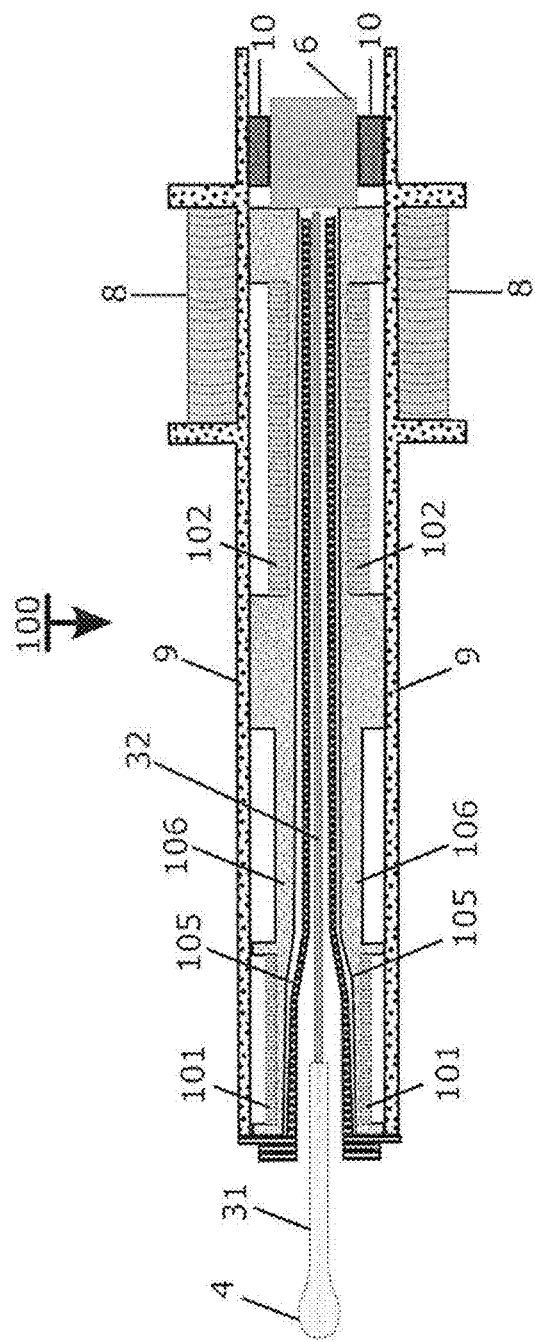
Figures 4A, 4B:
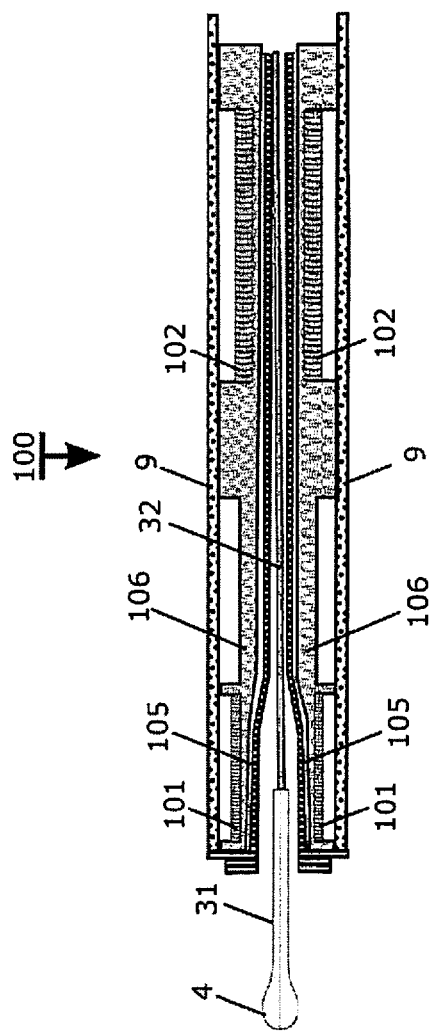

FIG. 1A presents a first type of a probe that can be used in the embodiments of a tonometer of the invention FIG. 1B presents a second type of a probe that can be used in the embodiments of a tonometer of the invention FIG. 1C presents a first embodiment of a tonometer of the invention, wherein the so holding mechanism is a magnet and the releasing actuator is a magnetic coil FIG. 2 presents a second embodiment of a tonometer of the invention, wherein the holding mechanism is a magnet and the releasing actuator is a magnetic coil FIG. 3 presents a third embodiment of a tonometer of the invention, wherein the holding mechanism is a magnet and the releasing actuator is a magnetic coil FIG. 4A presents a fourth embodiment of a tonometer of the invention, wherein the holding mechanism is a magnet and the releasing actuator is a magnetic coil FIG. 4B is a cross-sectional view of the magnet and the releasing actuator of FIG. 4

Figure 5:
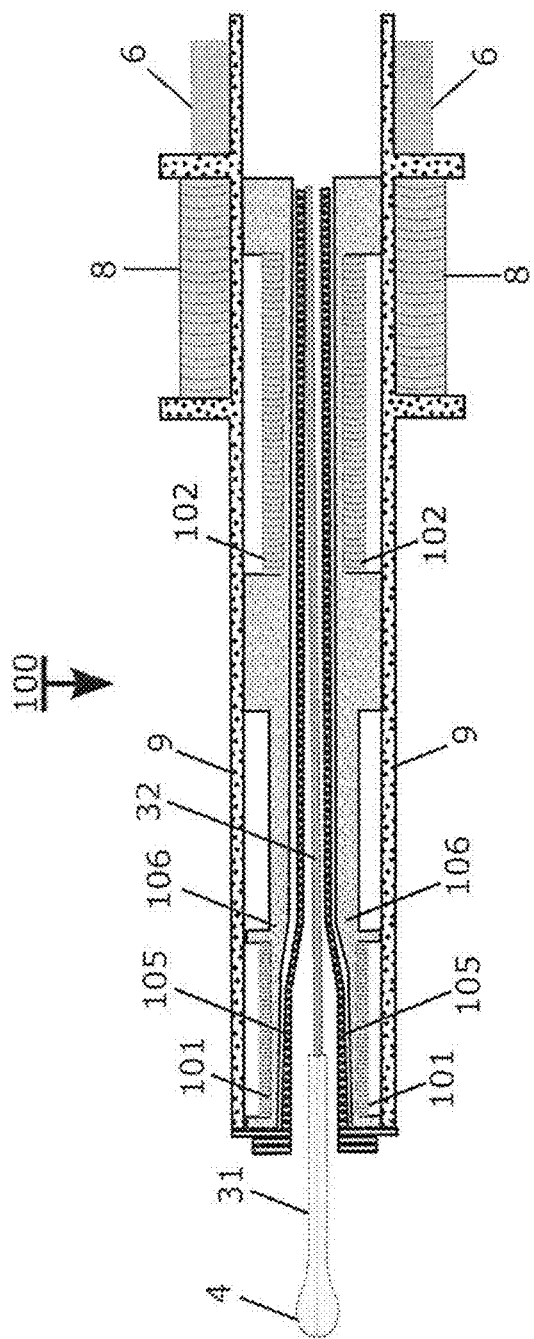
Figure 6:
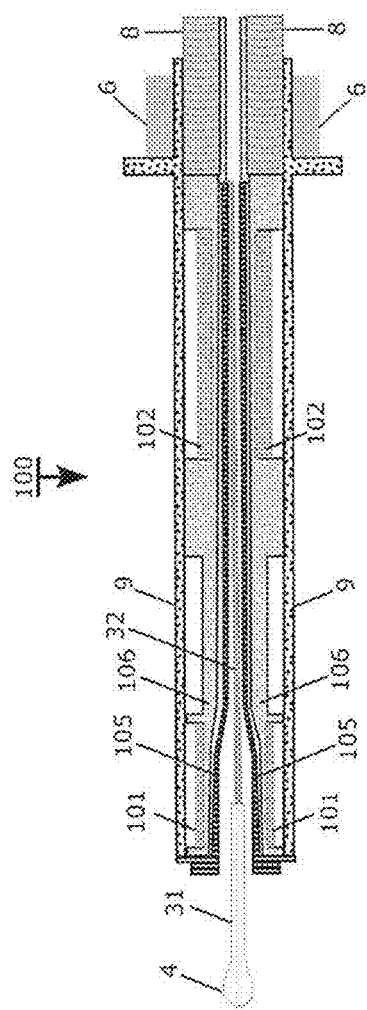
Figure 7:
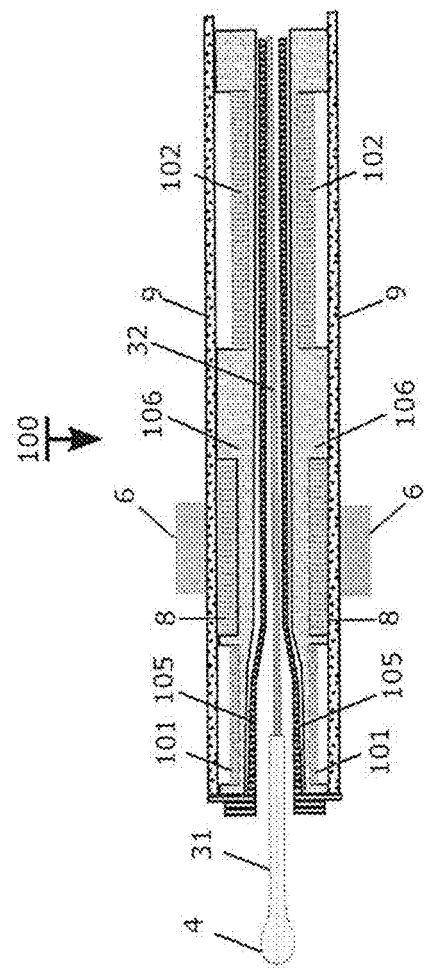
Figure 8:
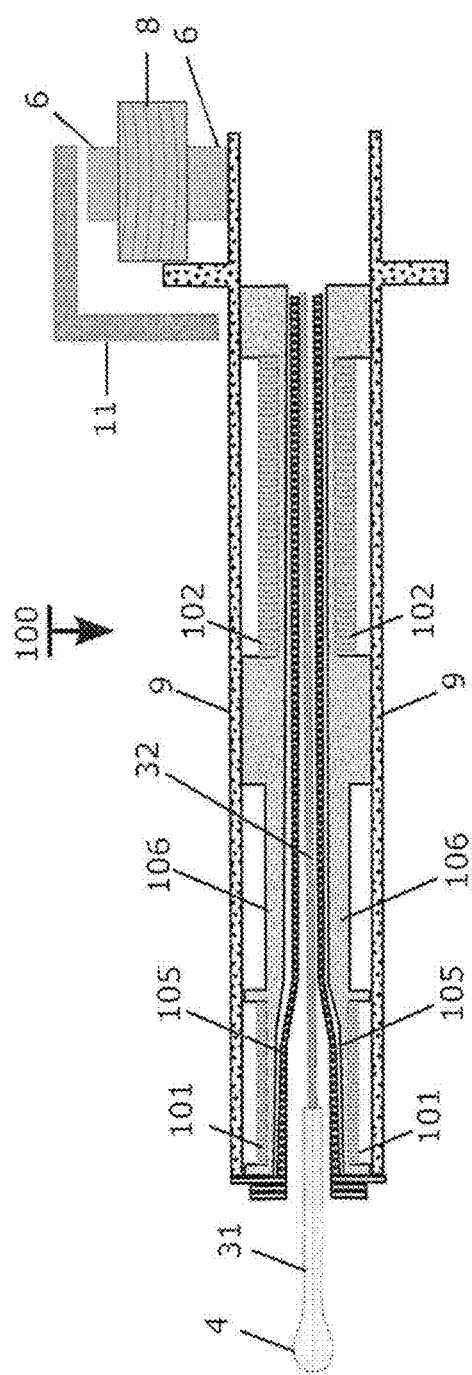
Figure 9:
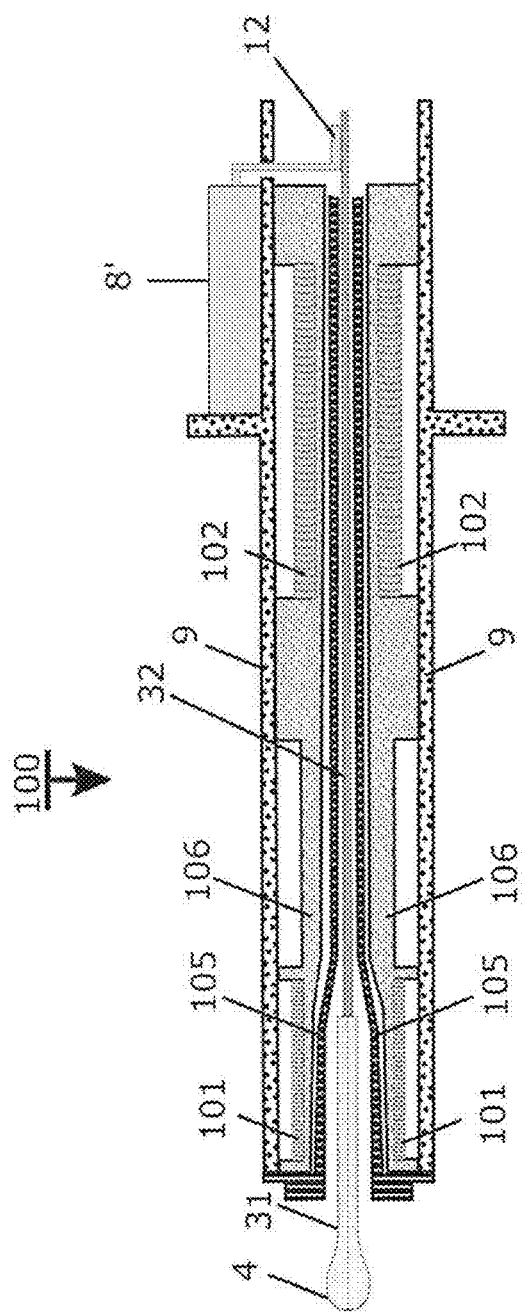
Figure 10:
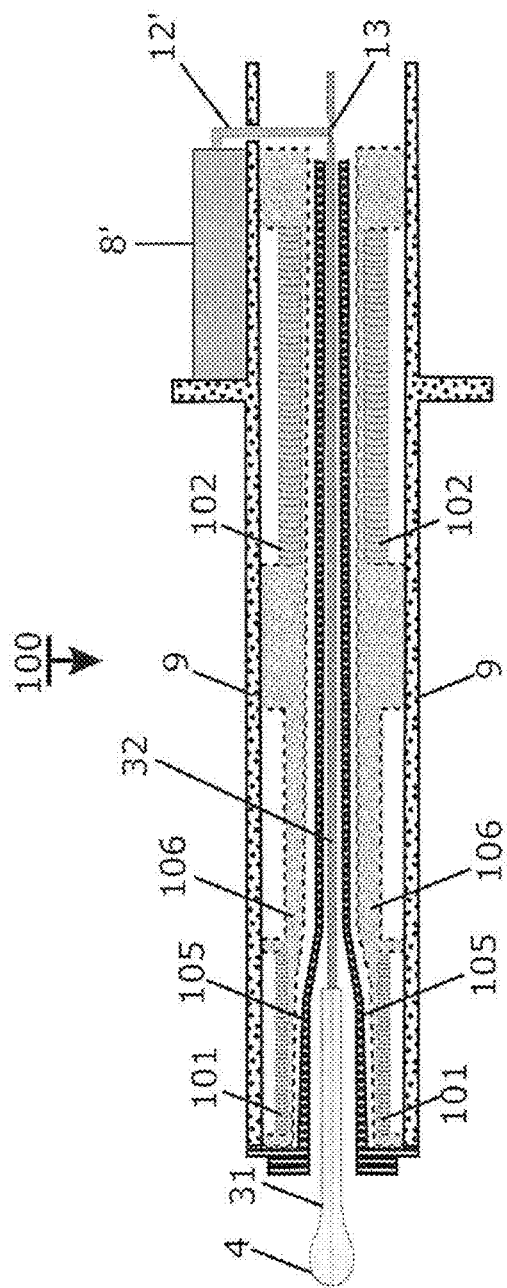

FIG. 5 presents a tonometer, wherein the holding mechanism is a friction brake caused by a magnet and the releasing actuator is a magnetic coil FIG. 6 presents a tonometer, wherein the holding mechanism is a friction brake caused by a magnet and the releasing actuator is a magnetic coil FIG. 7 presents a tonometer, wherein the holding mechanism is a friction brake caused by a magnet and the releasing actuator is a magnetic coil FIG. 8 presents a tonometer, wherein the holding mechanism is a friction brake caused by a magnet and the releasing actuator is a magnetic coil FIG. 9 presents a tonometer, wherein the holding mechanism is a friction brake caused by a solid object and the releasing actuator is a piezoelectric element, a pneumatic membrane, a hydraulic membrane or a magnetic coil FIG. 10 presents a tonometer, wherein the holding mechanism is a mechanical catch and the releasing actuator is a piezoelectric element, a pneumatic membrane, a hydraulic membrane or a magnetic coil

DETAILED DESCRIPTION

FIG. 1A presents a probe 3 that can be used in the embodiments of an apparatus of the invention for measuring intraocular pressure, i.e. in a tonometer. The probe 3 is formed of a rear part 32 of magnetic material, such as steel, and a front part 31 of non-magnetic material, such as a plastic material. The front part 31 of the probe 3 has a tip 4, which impacts the eye in the measurement of the intraocular pressure.

FIG. 1B presents a probe 3 that can be used in the embodiments of an apparatus of the invention for measuring intraocular pressure, i.e. in a tonometer. The probe 3 is partly of magnetic material and the probe 3 has a tip 4, which impacts the eye in the measurement of the intraocular pressure.

FIG. 1C presents a first embodiment of a functional part 100 of the tonometer of the invention, wherein the probe 3 of FIG. 1A and FIG. 1B can be used.

The functional part 100 together with other components belonging to a tonometer are inside a tonometer case. Examples of other components in the tonometer are means for adjusting the distance from which the probe is launched for impacting the eye, batteries, from which the apparatus gets its operating power, a circuit board on which the electronics of the apparatus are assembled, a display, a processing unit, and a socket, to which an external recharging device can be connected. The means for adjusting the distance can be an adjustable forehead support. Only the functional part 100 of the tonometer is presented in the figures. The above components of a tonometer are closer presented in WO publication 03/105681.

The functional part 100 has a frame pipe 9, inside which there is an inner tube around the probe 3, which is partly of magnetic material. The inner tube is hereafter referred to as the probe base 105.

The probe 3 is accelerated towards an eye by means of a driving inductive coil system 101 in the front end of the probe base 105. The force pushing the probe 3 is generated in the coil 101 by a voltage fed to the coil 101. So power is supplied to the front coil 101 causing the probe 3 to start moving and to impact the eye. Upon contact with the cornea of the eye, the probe 3 starts to decelerate and rebounds from the eye.

As a result, a voltage, which is dependent on the intraocular pressure, is induced in another coil 102. The coils 101 and 102 are mounted on a coil frame 106.

This voltage and other parameters, such as the speed of the probe 3, are detected by the rear coil 102 and recorded and processed with a data processing unit (not shown). The intraocular pressure is calculated by means of an algorithm from the measurement data of parameters of the moving probe 3 and the result is presented on a display of the tonometer.

The tonometer of the invention might also comprise means for correcting the measurement results in proportion to how much kinetic energy is lost or gained in the impact and rebound of the probe.

Instead of the front coil 101 giving the probe 3 the launching power, it is possible to use the rear coil 102.

One of the coils 101 and 102 are intended to operate also as a retainer for holding the probe 3 in place when the power is switched on in the tonometer.

After the impact has occurred and the measurement result has been obtained, there is a risk that the probe 3 detaches due to movements of the tonometer or for other reasons. This is prevented in the embodiment of FIG. 1C of the invention by using a magnetic circuit 6 (such as a magnet), which magnetic circuit 6 can be located behind the rear part of the probe base 105 (in the opposite end of the apparatus than the tip 4 of the probe 3). The magnetic circuit 6 holds the probe 3 inside the probe base 105 in any position of the apparatus once the probe 3 is loaded into the probe base 105.

The magnetic circuit 6 can consist of a permanent magnet. Means for releasing the probe, such as a releasing coil 8, is placed around the frame pipe 9 in order to cancel the effect of the magnetic circuit 6 during measurement. Consequently, the probe 3 can move. The frame pipe 9 works as a case in the functional part 100 of the apparatus.

When current is flown into the releasing coil 8 during measurement, the resulting magnetic field compensates the effect of the magnetic field of the magnetic circuit 6 and the probe 3 can move.

The control functions of the releasing coil 8 is integrated into the electric circuit board of the tonometer. The releasing coil 8 gets its power from the power supply and the currents flow in the releasing coil 8 and the driving coil 101 flow during a measurement.

The position, shape, dimensions, material, layers and turns of the magnetic coil are not fixed and can be adapted suitable case by case. Similarly, the position, shape, dimensions, material and grade of the magnet 6 are not fixed and can be adapted suitable case by case.

FIG. 2 presents a second embodiment of a tonometer of the invention. In this embodiment, the releasing coil 8 is wrapped around the frame pipe 9 like in the first embodiment of FIG. 1B but the frame pipe is split into two parts, i.e. a rear frame part 9A and a front frame part 9B.

FIG. 3 presents a third embodiment of a tonometer of the invention. The frame pipe 9 is in one part like that in FIG. 1C. A centralizing part 10 between the frame pipe 9 and the magnetic circuit 6 facilitates the mounting and keeping of the magnet 6 in place.

The embodiment of FIG. 4A otherwise corresponds to that of FIG. 1C but the releasing coil 8 is directly wound around the magnet 6, whereby the means 6 for holding the probe 3 inside the probe base 105 are integrated with the means 8 for releasing the probe 3.

FIG. 4B is a cross-sectional view of the magnet 6 around which the releasing coil 8 has been wound.

FIG. 5 presents a tonometer, wherein the holding mechanism is a friction brake caused by a magnet and the releasing actuator is a magnetic coil.

A magnet 6 generates a magnetic field and the probe 3 turns parallel to the field. Because of the turning, the probe touches the probe base 105, which causes friction between the contact areas of the probe 3 and the probe base 105. The friction prevents the probe 3 from moving and falling out from the device. During a measurement, current flows into the releasing coil 8 and the produced magnetic field compensates the effect of the magnetic circuit 6. Consequently, the probe can move.

FIG. 6 presents a tonometer, wherein the holding mechanism is a friction brake caused by a magnetic circuit 6 and the releasing actuator is a magnetic coil 8. Here the magnetic circuit 6 is on the frame pipe 9 of the functional part 100 and the releasing coil 8 is inside the frame pipe 9. The releasing coil 8 is outside the rear part of the coil frame 106.

FIG. 7 presents a tonometer, wherein the holding mechanism is a friction brake caused by a magnetic circuit 6 and the releasing actuator is a magnetic coil 8. Here the position of the magnetic circuit 6 is like in FIG. 6 around the releasing coil 8 with the frame pipe 9 there between, but the magnetic circuit 6 and the releasing coil 8 are in the front part of the functional part 100 between the driving coil 101 and the measuring coil 102.

FIG. 8 presents a tonometer, wherein the holding mechanism is a friction brake caused by a holding magnet and the releasing actuator is a magnetic coil. The releasing coil 8, which is around the magnet 6 is outside the rear part of the functional part 100, the combination being mounted on the frame pipe 9.

A magnet 6 generates a magnetic field which is guided via a magnetic material 11 placed in the vicinity of the magnet 6. The magnetic field affects the probe 3 and it tries to turn parallel to the field. Because of the turning, the probe 3 touches the probe base 105, which causes friction between the contact areas of the probe base 105 and the probe 3. The friction prevents the probe 3 from moving and falling out from the device. During a measurement, current flows in the releasing coil 8 and a produced magnetic field compensates the effect of the magnet 6. Consequently, the probe 3 can move.

FIG. 9 presents a tonometer, wherein the holding mechanism is a friction brake caused by a solid object and the releasing actuator is a piezoelectric element, a pneumatic membrane, a hydraulic membrane or a magnetic coil.

A solid object 12 is in contact with the probe 3 and causes friction between the contact areas of the probe 3 and the solid object 12. The friction holds the probe 3 so that it can not move or fall out from the device. During the measurement, the releasing actuator 8' shifts the solid object 12 so that it does not touch the probe 3 anymore. Consequently, there is no friction and the probe 3 can move.

The releasing actuator 8' is on the frame pipe 9 at the rear part of the functional part 100 and the solid object touches the rear end of the probe 3, which is partly inside the releasing actuator 8'.

FIG. 10 presents a tonometer, wherein the holding mechanism is a mechanical catch and the releasing actuator is a piezoelectric element, a pneumatic membrane, a hydraulic membrane or a magnetic coil.

There is a notch 13 in the rear part of the probe 3. A solid object 12' is placed on the notch 13 and these work together as a mechanical catch. The catch prevents the probe 3 from moving and falling out from the device. During the measurement, the releasing actuator 8' lifts the solid object 12' and the probe 3 can move.

The releasing actuator 8' is on the frame pipe 9 at the rear part of the functional part 100 and the mechanical catch is at the rear end of the probe 3.

The invention claimed is:

1. An apparatus for measuring intraocular pressure, comprising:
   a tubular probe base having a distal end configured to be oriented towards a surface of an eye, and a proximal end;
   a probe having a distal end contactable with the surface of the eye to derive an intraocular pressure in the eye from variations in a velocity of the probe, the probe being positionable at least partially inside the tubular probe base, and the probe being at least partly made of a magnetic material;
   an induction coil disposed adjacent the distal end of the tubular probe base and disposed radially outward of the tubular probe base, wherein actuation of the induction coil provides the probe with a specific velocity;
   a permanent magnet for holding the probe inside the tubular probe base, wherein the permanent magnet is located proximally of the proximal end of the tubular probe base and coaxially with the probe, a distal end of the permanent magnet is disposed proximally of a proximal-most end of the induction coil, wherein the permanent magnet is configured to hold the probe inside the tubular probe base absent power being delivered to the apparatus;
   a magnetic coil disposed adjacent the proximal end of the tubular probe base, and disposed proximally of the proximal-most end of the induction coil, an entirety of the magnetic coil is disposed radially outward of the permanent magnet, wherein the magnetic coil being actuatable separately of the induction coil, wherein actuation of the magnetic coil releases the probe from the hold imparted by the permanent magnet; and
   a measuring coil disposed in coaxial alignment with the induction coil and the magnetic coil and spaced apart from the induction coil and the magnetic coil, the measuring coil disposed radially inward of the magnetic coil and proximally of the proximal-most end of the induction coil, the measuring coil positioned to receive a voltage from the induction coil to determine the intraocular pressure based on the variations in the velocity of the probe, and the measuring coil being actuatable separately of the induction coil and the magnetic coil.

2. The apparatus according to claim 1, wherein the magnetic coil radially surrounds the proximal end of the tubular probe base.

3. The apparatus according to claim 1, further comprising a frame pipe, the tubular probe base being disposed within the frame pipe, the permanent magnet being fixed from movement relative to the frame pipe.

4. The apparatus according to claim 3, wherein the magnetic coil is wrapped around the frame pipe.

5. The apparatus according to claim 1, wherein a distal-most end of the permanent magnet and a proximal-most end of the magnetic coil are longitudinally aligned.

6. The apparatus according to claim 1, wherein the induction coil is configured to operate, when power is switched on in the apparatus, as a retainer for holding the probe in place.

7. The apparatus according to claim 1, wherein the apparatus is configured to correct measurement results in proportion to how much kinetic energy is lost or gained in an impact and rebound of the probe.

8. The apparatus according to claim 1, wherein the magnetic coil is wound around the permanent magnet.

9. The apparatus according to claim 1, wherein an entirety of the measuring coil is positioned distally of the permanent magnet.

10. The apparatus according to claim 1, wherein the magnetic coil, upon receiving a current, is configured to cancel an effect of a magnetic field of the permanent magnet to allow for movement of the probe.

11. The apparatus according to claim 1, wherein the measuring coil is disposed in coaxial alignment with the permanent magnet.

12. An apparatus for measuring intraocular pressure, comprising:
    a tubular probe base having a distal end configured to be oriented towards a surface of an eye, and a proximal end;
    a probe having a distal end contactable with the surface of the eye to derive an intraocular pressure in the eye from variations in a velocity of the probe, the probe being positionable at least partially inside the tubular probe base, and the probe being at least partly made of a magnetic material;
    an induction coil disposed in mechanical cooperation with the distal end of the tubular probe base, wherein actuation of the induction coil provides the probe with a specific velocity;
    a magnetic circuit disposed proximally of the proximal end of the tubular probe base and spaced from the induction coil, the magnetic circuit for holding the probe inside the tubular probe base, wherein the magnetic circuit is configured to hold the probe inside the tubular probe base absent power being delivered to the apparatus;
    a magnetic coil disposed radially outward of the tubular probe base, disposed radially outward of the magnetic circuit, and disposed proximally of the induction coil, the magnetic coil being actuatable separately of the induction coil, wherein actuation of the magnetic coil releases the probe from the hold imparted by the magnetic circuit; and
    a measuring coil disposed in coaxial alignment with the induction coil and the magnetic coil, disposed proximally of the induction coil, spaced apart from the magnetic coil, disposed radially inward of the magnetic coil, and disposed distally of the magnetic circuit, the measuring coil positioned to receive a voltage from the induction coil to determine the intraocular pressure based on the variations in the velocity of the probe, and the measuring coil being actuatable separately of the induction coil and the magnetic coil.

13. The apparatus according to claim 12, wherein the magnetic coil is located at the proximal end of the tubular probe base.

14. The apparatus according to claim 12, further comprising a frame pipe, the tubular probe base being disposed within the frame pipe, the magnetic circuit being fixed from movement relative to the frame pipe.

15. The apparatus according to claim 12, wherein the magnetic coil is wound around the magnetic circuit, the magnetic circuit being a permanent magnet.

16. The apparatus according to claim 12, wherein the induction coil is configured to operate, when power is switched on in the apparatus, as a retainer for holding the probe in place.

17. The apparatus according to claim 12, wherein the apparatus is configured to correct measurement results in proportion to how much kinetic energy is lost or gained in an impact and rebound of the probe.

18. The apparatus according to claim 12, wherein the induction coil is configured to induce a voltage in the measuring coil.

19. The apparatus according to claim 12, wherein the magnetic coil, upon receiving a current, is configured to cancel an effect of a magnetic field of the magnetic circuit to allow for movement of the probe.

* * * * *